United States Patent [19]

Saleeb et al.

[11] Patent Number: 5,219,602
[45] Date of Patent: * Jun. 15, 1993

[54] AQUEOUS CALCIUM CITRATE COMPOSITIONS

[75] Inventors: Fouad Z. Saleeb, Pleasantville; Susan M. Vidal, Patterson, both of N.Y.

[73] Assignee: Kraft General Foods, Inc., Northfield, Ill.

[*] Notice: The portion of the term of this patent subsequent to Sep. 22, 2009 has been disclaimed.

[21] Appl. No.: 811,192

[22] Filed: Dec. 20, 1991

[51] Int. Cl.⁵ ............................................. A23L 1/275
[52] U.S. Cl. ................................... 426/250; 562/584; 426/96; 426/302; 426/531; 426/540; 426/549; 426/579; 426/582; 426/589; 426/603
[58] Field of Search .................. 562/584; 426/96, 250, 426/302, 531, 540, 549, 579, 582, 589, 603

[56] References Cited

U.S. PATENT DOCUMENTS 5,149,552 9/1992 Vidal et al. .......................... 426/321

OTHER PUBLICATIONS

Hawley, The Condensed Chemical Dictionary, 10th Ed., 1981, Van Nostrand Reinhold Co.: New York, p. 180.

Primary Examiner—Joseph Golian
Attorney, Agent, or Firm—Linn I. Grim

[57] ABSTRACT

An aqueous dispersion containing a finely divided reaction product of a calcium compound with citric acid having a mole ratio of calcium to citric acid from 2.5:2 to 2.95:2 is provided to be used for opacifying and whitening aqueous food compositions.

29 Claims, No Drawings

AQUEOUS CALCIUM CITRATE COMPOSITIONS

This invention relates to aqueous compositions comprising certain calcium citrate salts and the use thereof, particularly in the food industry.

CROSS-REFERENCE

Commonly assigned U.S. patent application Ser. No. 07/704,500 filed May 23, 1991, now U.S. Pat. No. 5,149,552 issued Sep. 22, 1992 which describes certain calcium citrate salt crystals.

BACKGROUND OF THE INVENTION

The dietary importance of low-fat, low-calorie, no cholesterol foods is well-documented in not only the scientific literature but also in the lay press. Considerable research effort has been, and is now being, expended to meet the requirements of new food technology. Thus, low fat food products such as cheeses, mayonnaise, pudding, pastries, salad dressings, margarines and the like have been developed based on non-fat substitutions in whole or in part for the fat content of classical foods. Such products necessitate new food additives and constituents of the new dietary food compositions. These new additives and constituents are mainly designed to improve appearance, color, mouth-feel, and induce other properties to assure public acceptability of the new dietary compositions. To be successful, such additives and constituents should be food acceptable and compatible with the compositions in which they are employed. For example, titanium dioxide has been used as a whitener in low fat compositions and is found to be compatible in these compositions. However, the food-acceptability of titanium dioxide has been challenged and is rejected in many countries, especially in Europe.

SUMMARY OF THE INVENTION

The present invention provides new and useful aqueous dispersion calcium citrate salt compositions which are readily adaptable for use in food compositions, particularly as opacifiers, whitening agents, texture modifiers and partial fat substitutes. These and other uses of the present new salt compositions are described hereinafter.

DETAILED DESCRIPTION OF THE INVENTION

The present new aqueous compositions comprise a finely divided "reaction product of a calcium compound selected from the group consisting of calcium hydroxide, calcium oxide and calcium carbonate with citric acid wherein said reaction product has a mole ratio of calcium to citric acid from 2.5:2 to 2.95:2, the dry form of the salt containing not greater than 6% water dry weight, and an aqueous slurry (1% by weight) of said salt in water at 25° C. showing a pH value of from about 4 to about 7, and preferably from about 4 to about 5.5.

In general, these calcium citrate crystals are prepared by spray drying a neutralization mixture prepared by neutralizing citric acid with a slurry of calcium carbonate or calcium oxide or hydroxide in water, e.g., a slurry of calcium hydroxide under controlled conditions to assure the production of the present new calcium citrate salts. Temperature, slurry solid content, rate of mixing of reactants and agitation time before spray drying are critical parameters in determining the physical characteristics of final product.

In particular, the calcium citrate crystals are prepared by first neutralizing citric acid with calcium hydroxide while controlling the rate and conditions of the reaction as well as the degree of neutralization. In the present process, a calcium hydroxide aqueous slurry is reacted with a citric acid solution in water resulting in a strong exothermic reaction. The rate of reaction, concentration of reactants and varying conditions are all important factors in producing calcium citrate salts of the desired pH values, moisture content and particularly the desired particle size.

It is preferred to form two separate aqueous systems, one, a solution of citric acid and the second, a slurry of calcium hydroxide, oxide or carbonate and then mix the uniform slurry of calcium hydroxide or carbonate with the aqueous citric acid. The temperature of the mixture is not allowed to exceed about 60° C. The pH of the slurry so produced after thorough mixing should fall within the range of 4–6 and, if needed, should be adjusted to this range of pH. The slurry can be used as such or can be spray-dried or dried by other known drying steps.

The produced calcium citrate salt is very insoluble in water providing about 0.1% by weight solution at ambient temperature and slightly more soluble in hot water. During preparation of a batch and while waiting for spray drying of the batch, the salts are present in the insoluble form, a slurry of tiny crystals which form aggregates of varying particle size ranging from 5 to 100 microns. In present experience, the best products are obtained by using the following conditions.

The solids level of the aqueous slurry of calcium citrate salt is maintained at 20–26% and preferably at 22–24% by weight based on anhydrous salt. The slurry temperature during spray drying is from 80° C.–100° F. and preferably 80°–90° F. To avoid gel formation in the aqueous slurry, especially at temperatures below 70° F., and recrystallization which can occur on prolonged storage, spray drying of the aqueous slurry is effected within about 4–5 hours after slurry preparation. The slurry is spray dried at an inlet temperature of from about 425° F. to about 460° F. to deliver a free-flowing white powder with a moisture content of less than 6% and bulk density of from about 0.3 to about 0.7 g/cc. Extensive mixing and especially homogenization prior to spray drying should be avoided since the particles of salt may be broken down into fine particles.

The calcium citrate crystals generally have the following characteristics:

| | |
|---|---|
| Bulk Density | 0.33–0.66 g/cc |
| Granulation | 95% through U.S. 100 mesh or 150 microns |
| Rotatap, 8 min. | 10% maximum through U.S. 400 mesh or 38 microns |
| pH (1% by weight solution) | 4.0–6.5 |
| Appearance | free-flowing, white powder |

These salts are neutral or slightly acidic and have a well-defined crystal size. The salt can be employed in the form of the anhydrous salt or the hydrated salt. In the hydrated form, the salt can usually contain up to about 13–15% by weight of water of hydration. In general, it is preferred to use the salt in lower hydrated form with less than about 10% by weight of water of hydration. Of course, the hydrated salt can be dried to any level of water of hydration using known methods. On standing, the salt does not undergo any loss or gain of water during storage.

The concentration of salt in the present new compositions can range from about 0.2% to about 22% by weight of the composition. Particularly desirable are compositions wherein the concentration of salt is from about 15% to about 20%. Such compositions have a high ratio of salt to water and can be used most efficiently in providing desired levels of the salt in the food compositions to which they are added, as described hereinafter.

The calcium citrate employed in the present invention is in the form of small platelet crystals. The average length of the crystals is below 3.0 microns, preferably about 1.5 microns, width below 2.0 microns, preferably about 1 micron and thickness below 1 micron, preferably 0.1 to 0.2 micron. During preparation, clusters of these tiny platelets aggregate together to form spherical particles that range from about 2 to about 50 microns in diameter. Such clusters are readily separable by mechanical stirring in water of by merely allowing the clusters to stand in water for protracted periods of time, e.g. overnight at room temperature. A most efficient method for reducing the clusters to the individual platelets is the use of mechanical shear, as provided by a ball mill. Other mechanical stirring means that can be employed include homogenizers, microfluidizer or colloid mills, but the ball mill product is smoother and more viscous at a given salt/water content.

When mixed with water, particularly at levels above about 10% by weight, the present spray-dried calcium citrate salt platelets cause a significant increase in the viscosity of the mixture. Thus, at 15% to 20% by weight the aqueous calcium citrate compositions are in the form of thick pastes resembling soft cheeses and margarines in consistency. At 20% and higher levels, the mixtures tend to solidify, especially when highly efficient mechanical shear is used.

In one preferred modification, the calcium citrate platelets are coated with a water-dispersible, food-acceptable additive capable of coating the platelets. A wide variety of such coating additives can be used for this purpose and include, for example, protein coatings such as casein, sodium caseinate and zein; polysaccharide gums such as xantham gum, gum arabic, locust bean gum, guar and similar gums; higher fatty acids, e.g. $C_{12}$-$C_{22}$ such as lauric acid, stearic acid, oleic acid, linoleic acid, or sodium or potassium salts of these higher fatty acids; natural food solids such as starches and skim milk solids and fruit juices such as orange juice solids; and modified cellulose gum such as methyl cellulose, ethyl cellulose and carboxymethyl cellulose. Coating of the calcium citrate platelets can be effected during preparation of the present new aqueous compositions by the mere expediency of adding the coating agent to the water of the present new aqueous compositions prior to or during preparation by intimate mixing of the salt with water. Alternatively, before spray-drying of the calcium citrate suspension in water during preparation of the new salt, the water-dispersible coating agent can be added to the reaction mixture and the spray-dried product obtained in coated form. A further procedure involves addition of the coating agent to the food composition to which the present new food additive aqueous compositions are added and the salt platelets are coated in situ during dispersion in the food composition.

The present new aqueous compositions are particularly effective as opacifier and whitening agents for aqueous food compositions. Exemplary such food compositions include puddings, mayonnaise, salad dressings and similar products in which oil is replaced by water and other food ingredients and the products are described as non-fat or low-calorie foods. When used as an opacifier-whitener, the levels of salt should be from about 0.2% to 5.0% of the food composition.

To attain such levels of salt for opacifier-whitener uses, the salt can be added neat to the water used to form the aqueous food composition or directly to the aqueous food composition. Alternatively, and preferably, the salt is added in the form of the new aqueous calcium citrate pastes of this invention. The use of the paste assures the highly desirable form of platelets of the calcium citrate which are responsible for the opacifier-whitener results in the aqueous food composition. The paste is preferable comprised of from about 15% to about 20% by weight salt.

In either form of addition, the calcium citrate crystals are distributed uniformly throughout the food composition by usual mixing methods and no special handling is required to accomplish this result.

In addition to use as a whitener and opacifier, the present new aqueous salt compositions are useful as potential fat substitutes due to the fat mimetic property thereof. This use may be restricted due to chalky taste of the calcium citrate crystals and is preferably restricted to not greater than about 5% by weight and most preferably less than about 3% of salt based on the finished composition.

A further use of the present new aqueous calcium citrate compositions is as an anti-sticking agent, particularly for baking products such as cookies, breads and cakes. In this use, the aqueous paste is merely applied to the surface of baking trays in contact with the product to be baked and serves as an effective anti-sticking agent. The layer of paste applied can be a very thin layer formed by merely spreading the aqueous salt composition substantially uniformly across the baking surface. The baked products are easily removed without contact surface disruption. Even of greater significance is the avoidance of fat-based anti-sticking coatings on the baking surface with the accompanying inclusion of the fat coating in the baked product.

The present new aqueous dispersions of calcium citrate have also been used in place of roll-in margarine for the production of fat-free baked goods without adversely affecting appearance, taste or size of the baked products when compared with products made with margarine. As is well known, margarine is comprised of hydrogenated oils which contain trans fatty acids.

In contrast with the results obtained with the calcium citrate crystals of this invention commercial calcium citrate, whether in hydrated form (13% $H_2O$) or after rigorous drying, does not exhibit the same properties and is ineffective when tested side-by-side with the present new compositions, or as an additive to aqueous food composition. Without being bound to any theory of operation of the present invention, the phenomena observed with the present new salts is attributable to the particle size of the salt crystals, relying almost completely on the shape, number and geometrical arrangement of the calcium citrate crystals as they disperse in the water phase of the new food compositions of this invention.

The following examples are proved to further illustrate the invention.

EXAMPLE 1

A calcium citrate sample was prepared by reacting 2763.8 lbs. of citric acid with 1600 lbs. calcium hydroxide (97–98% $Ca(OH)_2$ by analysis) in the presence of 1433 gallons of water. The mole ratio of calcium hydroxide to citric acid was very slightly less than 3:2, actually 2.92:2. The citric acid (Pfizer fine granular, food grade) was mixed in a large batch tank with 675 gallons of cold water. The calcium hydroxide (Mississippi Lime, hydrated lime food code) was mixed in a separate batch tank with 675 gallons of cold water. The calcium hydroxide slurry is then pumped into the citric acid solution at a rate to deliver the entire slurry in 10–15 minutes. It is necessary to have good agitation during the entire reaction and mixing process. The remaining 83 gallons of water is used to rinse the calcium hydroxide tank and transport lines. Due to the heat of reaction, the temperature of the resultant slurry was increased from an initial value of 15° C. (60° F.) to a maximum of 57° C. (134° F.). After the reaction is complete, the batch is cooled to 80°–90° F. The final pH of this concentrated slurry (22% calcium citrate, dry basis) should fall within the range 3.8–4.6 or can be adjusted up or down using the reacting ingredients. The slurry is then dried via spray drying utilizing a rotary wheel (7600 rpm). The outlet temperature was adjusted to 225° F. and the inlet temperature was 450° F.

The calcium citrate powder obtained after spray drying was a free-flowing white powder with a moisture less than 6.0% and a bulk density in the range 0.33–0.65 g/cc. The pH of 1% slurry in water was 5.5. 95% of the powder passed through U.S. 200 mesh.

EXAMPLE 2

Spray-dried calcium citrate produced in accordance with Example 1 was mixed with water and then micromilled to obtain a fairly thick paste which does not require refrigeration using the following procedure.

Calcium citrate (2265 g.) was added to 9656 g. of water at room temperature. A fairly gritty slurry was obtained (19% calcium citrate, 81% water) that was maintained in suspension by using an electric stirrer. The suspension was then pumped and milled using a Dyno-Mill filled with glass beads (Type KDL, manufactured by Willy A Bachofen, AG Machinenfabrik, Basel-Switzerland). One pass through the Dyno-Mill was sufficient to produce a fairly smooth paste. This sample is stable for several months whether refrigerated or stored at room temperature. There was no crystal growth or loss of smoothness.

EXAMPLE 3

The procedure of Example 2 was repeated but with 1% sodium caseinate added to the water used to produce a product in which the calcium citrate is coated with the sodium caseinate.

The product is smoother with a more shiny appearance due to the sodium caseinate coating. Again a paste type texture was obtained when the calcium citrate (19 weight percent) was micromilled in an aqueous phase.

If not pasteurized, the product requires refrigeration.

EXAMPLE 4

The precipitated calcium citrate produced in accordance with Example 1 without spray drying was coated with sodium caseinate using the procedure of Example 3 to obtain a product of the following composition:

22% calcium citrate
1.1% sodium caseinate
76.9% water

This sample also requires refrigeration, if not pasteurized.

To produce this product, 1920 g. of anhydrous citric acid was dissolved in 6000 ml. water. Sodium caseinate (143 g.) (Alanate 155, New Zealand Milk Products) was dissolved in 1500 ml. hot water; this solution was then cooled to room temperature and mixed with the citric acid solution. A slurry of 1110 g. of calcium hydroxide in 1870 ml water was added quickly with stirring to the citric acid-sodium caseinate solution. Within two minutes of mixing, the temperature of the mixture increased from 70° F. to 150° F. A coarse caseinate-coated calcium citrate suspension was obtained that was continually stirred for about 45 minutes. During this period, the temperature dropped to 100° F. The suspension was homogenized for 10 minutes using a Ross laboratory homogenizer followed by one pass through the Dyno-Mill as in Example 2. The homogenization step facilitated the even pumping of the suspension through the Micromill.

A fairly viscous, smooth and shiny paste was obtained.

EXAMPLE 5

An oil-free mayonnaise was prepared with the following composition:

| | |
|---|---|
| water | 642.1 g. |
| whole egg | 113.5 g. |
| starch | 60.5 g. |
| sugar | 46 g. |
| vinegar | 30 g. |
| dry egg white | 29.9 g. |
| maltodextrin | 19.7 g. |
| lemon juice | 18.1 g. |
| salt | 10 g. |
| gums | 2.69 g. |
| flavor | as needed |

To each of five samples of this oil-free mayonnaise was added:

(a) titanium dioxide (0.38%) control.

(b) The Example 1 spray-dried calcium citrate (2% salt)

(c) calcium citrate paste micromilled at the level of 19% in $H_2O$ using the Dyno-mill. The paste was added at the level of 10 parts per 100 parts mayonnaise (1.73% salt)

(d) calcium citrate micromilled in $H_2O$ in the presence of 1% sodium stearate and added at the level of 15 g./150 g. mayonnaise (1.73% salt)

(e) calcium citrate (19 parts) micromilled in 80 parts $H_2O$ and 1 part sodium caseinate. Ten grams of this paste was added to 100 g. of mayonnaise (1.73% salt)

In all cases, samples b–e exhibited an opacifying effect on the mayonnaise substantially the same as sample a ($TiO_2$). When compared to the mayonnaise mixture containing no opacifier additive, the samples a–e were quite opaque.

EXAMPLE 6

An instant pudding was prepared from the following dry blend:

| | |
|---|---|
| sugar | 75 g. |
| pregelatinized starch | 20 g. |
| sodium pyrophosphate | 2 g. |
| sodium orthophosphate | 2 g. |
| mono and diglyceride emulsifiers | 0.5 g. |
| vanilla flavor | as needed |

These ingredients were combined with 500 ml. of skim milk. After shaking for one minute, the resultant product was poured in 2 cups to set. The pudding lacked opacity and the appearance of a good quality appetizing product.

An opaque pudding was produced by dispersing 1.2 g. of spray dried calcium citrate (the Example 1 product) into the dry blend described above and the product produced by the same procedure.

Better opacity was obtained when the spray-dried calcium citrate of Example 1 was first mixed with water (19:81) and micromilled using a Dyno-mill and then 6.3 g. of the micromilled salt paste (1.2 g. calcium citrate) was dispersed in the skim milk with the dry blend being then added.

In both cases, the calcium citrate addition was at a level of 0.2% which did not adversely affect the texture or eating quality of the pudding but did greatly enhance the appearance and opacity of the product.

EXAMPLE 7

The spray dried product of Example 1 when mixed with water at from room temperature up to about 70° C. swells and with shear it increases the viscosity of the blend quite rapidly due to the breakdown of the crystal clusters described hereinbefore.

Sodium caseinate was dissolved in water at a level of 1% up to 5%. Spray-dried calcium citrate produced according to Example 1 was then added to a level of 18 to 20 parts by weight to the caseinate solution. The suspension was then mixed and then sheared in a homogenizer to produce a product with a viscosity higher than mayonnaise.

This procedure can be repeated with skim milk or regular milk in lieu of plain water to obtain milk products of high viscosity. When employed to produce products such as non-fat mayonnaise or milk products such as various cheeses, flavorants may be added to the aqueous system at any point in the preparation of the final food product. In addition, pH adjustments of the aqueous systems can be effected by addition of food grade reagents, e.g. citric acid, to provide desired pH levels. As indicated herein, the pH of the calcium citrate produced in Example 1 procedures is in the range of 4.5 to 6.0 depending on concentration. Other additives present in the aqueous composition may also affect the pH.

Various aqueous calcium citrate compositions were prepared and the stability of these compositions determined, as shown in the following Table where the respective parts of tricalcium citrate and coating, if present, are indicated, the balance being water.

| | Tricalcium Citrate (in parts per 100 of aqueous composition) | Coating | Observations |
|---|---|---|---|
| (a) | 13.5 | 0 | Remained pasty for months |
| (b) | 20 | xantham Gum (0.3) | Remained pasty for months |
| (c) | 18 | sodium stearate (0.13) | Remained pasty for months |
| (d) | 18.9(I) | gum arabic (1.89 and orange juice solids (2.45) | Remained pasty for months, yellow tint and glossy. |
| (e) | 18.9 | gum arabic (1.89) and orange juice solids (2.45) | same as (d) |
| (f) | 19 | pineapple juice solids (7.9) | |

Note I: precpitated calcium citrate produced as in Example 1 without spray-drying.

For samples a,b,c,e and f, the calcium citrate used is the spray dried product of Example 1, treated as indicated for each sample.

In the foregoing examples, the original crystals produced in accordance with Example 1 range from 0.5 to 1 micrometer. However, during actual precipitation and handling, these crystals may form clusters that grow in size up to 50 micrometers. Thus, some kind of post grinding or high shear is recommended to reverse cluster formation. The Dyno-mill is particularly well-adapted for the purpose of producing optimum size reduction. The microfluidizer or the colloid mill are other typical particle size reducing equipment.

When the procedures of Examples 4-6 were repeated with a homogenizer, e.g. Ross homogenizer, in lieu of the Dyno-mill, the resulting products were not always as smooth as those obtained with the very efficient Dyno-mill, ball mill.

When the shearing method is very effective, the resulting product may tend to become a solid mass when high levels of calcium citrate are used, e.g. more than 20:80 H$_2$O. Reducing the level of calcium citrate will obviate this problem.

EXAMPLE 8

Cheese

A fat-free/processed cheese loaf without opacifiers added was obtained. The opacifier calcium citrate was used to impart whiteness to the product in the following manner.

100 g of the processed cheese was transferred to a 300 ml beaker and 16 g of micromilled tricalcium citrate paste (19% TCC, 81% water) produced in accordance with Example 2 was added to the cheese block. The beaker was covered by Saran Wrap and microwaved for a total time of 60 seconds. It was mixed lightly at 30 sec. and then given a good mixing with a spatula at the end of the microwave treatment. The melted cheese was then covered and let stand to cool at room temperature. The weight of dry TCC in final product=2.6%.

To 100 g of the same processed cheese was added 3 g of spray dried calcium citrate of Example 1. The same melting/mixing procedure was followed exactly as in Sample 1 above.

As controls, a 100 g block of the starting unopacified cheese was used as well as a commercially available cheese containing the opacifier titanium dioxide.

The cheeses treated with calcium citrate are definitely very white (opaque) as compared with the original untreated cheese starting material. The experimental samples are as opaque as the titanium dioxide treated cheese and all treated samples look much better than the untreated cheese.

EXAMPLE 9

Salad Dressing

A buttermilk dressing dry mix was prepared from

| Whey Solids, sweet | 25.0 g |
|---|---|
| Gum arabic | 12.5 |
| Lactic acid | 4.2 |
| Salt | 15.7 |
| Buttermilk | 10.0 |
| Sugar | 7.5 |
| Citric acid | 1.8 |
| Xanthan gum | 0.5 |
| Flavor/spices | As needed |

These ingredients were mixed thoroughly and the blend was subdivided into four equal portions by weight. To two of them was added 2 g each of clouding agents TiO2 (titanium dioxide) as controls. To the other two portions was added to each 5 g of our spray dried clouding agent calcium citrate, (Example 1 product). These are the test samples.

One control and one test dry sample were mixed each with a mixture of one cup of Kraft Mayonnaise and one cup of skim milk. Both dry samples produced on reconstitution fairly thick dressings. No significant differences in opacity (white color) and other physical/taste attributes can be noticed between the TiO2 control and the test sample product.

The two remaining dry mix samples (TiO2 control and text sample) were blended each with two cups of water. Fairly fluid dressings were obtained as compared with these prepared using the mayonnaise and skim milk blend above, but the opacity of these two water bases are almost undistinguished. An unexpected result was that the calcium citrate remained in suspension much longer than the fairly dense TiO2 in the fluid (non viscous) dressing. It is clear that the present calcium citrate salt can replace TiO2 as an opacifier in a salad dressing whether a viscous or a fairly fluid dressing is needed. The pH of these dressings was 3.7 for the water substrate and 4.1 for the mayonnaise skim milk system.

EXAMPLE 10

Non-Fat Release Agents for Baked Goods a) 200 g of spray dried calcium citrate of Example 1 was weighed and added to 881 g of deionized water and thoroughly mixed to obtain an 18.5% calcium citrate paste. This sample was then passed through the Dyno-Mill three times. Kimwipe was used to apply a small thin coat of the milled material to the outer surface of an aluminum foil before applying a bread dough. After baking, there was no stickiness of product to the surface of the coated aluminum foil (easy release).

b) 200 g of the same calcium citrate was added to 800 g of deionized water and 0.3 g of Xanthan gum. Sample was used and dispersed without heating and micromilled as in a). Sample was similarly coated on aluminum foil as in a). Significant stickiness of product to aluminum foil was found after baking with this coating.

c) 400 g of the same calcium citrate and 4 g of sodium stearate were added to 1824 g of deionized water and micromilled. The resultant material was coated on aluminum foil as described in a). The dough was applied and after baking, there was no stickiness of the baked product to the surface of the coated aluminum foil.

d) Dough was applied to the untreated surface of the aluminum foil as a control. After baking, significant stickiness was found between this product and the foil.

e) A commercial fat-containing releasing agent, PAM, was sprayed on the aluminum surface and dough was applied and baked. No stickiness of product to aluminum foil was found.

It is evident that untreated calcium citrate (Example a)) or calcium citrate made more hydrophobic with sodium stearate (Example c)) act as non-fat release agents for baked goods.

EXAMPLE 11

Replacement for Roll-In Margarine in Baked Goods

Micromilled calcium citrate of Example 4 (348 g) was spread over a Sweet Danish dough (1500 g) and rolled in. The sample was then retorted for 30 minutes, flattened and rolled. This procedure was repeated three times in order to for multiple layers. The viscosity of the micromilled calcium citrate sample was high enough (close to roll-in margarine) that there was no squeezing of paste out of the dough.

The dough was then made into Swiss Rolls and proofed for 45 minutes. The dough was baked for 20 minutes. After baking and allowing to cool to room temperature, the Swiss rolls that resulted were stored in boxes at room temperature. Samples were compared to control made with margarine the second day. There was no discernible difference found between the margarine control and that made with micromilled calcium citrate in appearance, taste, and baked size.

This example shows that calcium citrate aqueous paste compositions can be used to replace margarine, a hydrogenated oil that is highly saturated with trans fatty acids. In addition, the calcium citrate sample would provide no extra fat calories since equal weight of margarine and TCC were used to produce the Sweet Danish.

What is claimed is:

1. An aqueous dispersion comprising from about 0.2% to about 22% by weight of a finely divided reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C.

2. A dispersion according to claim 1 wherein the mole ratio of calcium to citric acid is from about 2.61:2 to about 2.92:2.

3. A dispersion according to claim 1 wherein a 1% water slurry of said reaction product shows a pH value of from about 4 to about 5.5.

4. A dispersion according to claim 1 wherein the amount of said salt is from about 15% to about 20% by weight of the composition.

5. A dispersion according to claim 1 wherein said reaction product particles are coated with a food-acceptable additive.

6. A dispersion according to claim 1 wherein said reaction product being in the form of small platelets of a length of below about 3 microns, a width of below about 2 microns and a thickness of below about 1 micron.

7. A dispersion according to claim 6 wherein the average length of the crystals is about 1.5 microns, average width is about 1 micron and the average thickness is from about 0.1 to about 0.2 micron.

8. A dispersion according to claim 6 wherein said reaction product particles are coated with a food-acceptable additive.

9. An aqueous food composition comprising an aqueous dispersion of claim 42, said reaction product in claim 1 being present at a level from about 0.2% to about 3% by weight of the composition.

10. A composition according to claim 9 wherein the mole ratio of calcium to citric acid is from about 2.61:2 to about 2.92:2.

11. A composition according to claim 9 wherein a 1% water slurry of said reaction product shows a pH value of from about 4 to about 5.5.

12. An aqueous food composition of claim 1 said reaction product in claim 42 being present at a level from about 0.2% to about 3% by weight of the composition, said reaction product being in the form of small platelets of a length of below about 3 microns, a width of below about 2 microns and a thickness of below about 1micron.

13. A composition according to claim 12 wherein the average length of the crystals is about 1.5 microns, average width is about 1 micron and the average thickness is from about 0.1 to about 0.2 micron.

14. A composition according to claim 12 wherein said calcium citrate salt particles are coated with a food-acceptable additive.

15. A composition according to claim 12 which comprises salad dressing.

16. A composition according to claim 12 which comprises cheese.

17. A composition according to claim 12 which comprises pudding.

18. A composition according to claim 12 which comprises margarine.

19. A composition according to claim 12 which comprises mayonnaise.

20. A process of opacifying and whitening an aqueous food composition which comprises intimately mixing an opacifying and whitening amount of a finely divided reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C.

21. A process according to claim 20 wherein the opacifying and whitening amount of said reaction product is from about 0.5% to about 3% by weight of the composition.

22. A process according to claim 20 wherein said reaction product is in the form of small platelets of a length below about 3 microns, a width below about 2 microns and a thickness below about 1 micron.

23. A process according to claim 20 wherein said reaction product is in the form of small platelets of an average length of about 1.5 micron, average width of about 1 micron and average thickness of about 0.2 micron.

24. A process according to claim 20 wherein said reaction product is coated with a food-acceptable additive.

25. The process of producing finely-divided crystals of a reaction product of calcium hydroxide, calcium oxide and calcium carbonate with calcium citrate which comprises reducing crystal agglomerates of said reaction product wherein said reaction product has a mole ratio of calcium to citric acid from 2.5:2 to 2.95:2 in an 1% water slurry at a pH of from about 3.5 to about 7.0 to the form of small platelet crystals of a length of below about 3 microns, a width of below about 2 microns and a thickness of below about 1 micron.

26. A process according to claim 25 wherein said crystal agglomerates are reduced by grinding.

27. A process according to claim 25 wherein said crystal agglomerates are reduced by agitation in an aqueous medium for sufficient time to effect the desired reduction.

28. A process according to claim 25 wherein said crystal agglomerates are reduced by standing in aqueous medium for sufficient time to effect the desired reduction.

29. A process according to claim 25 wherein said crystal agglomerates are reduced by homogenizing in aqueous medium.

* * * * *

UNITED STATES PATENT AND TRADEMARK OFFICE
CERTIFICATE OF CORRECTION

PATENT NO. : 5,219,602
DATED : June 15, 1993
INVENTOR(S) : Fouad Z. Saleeb, et. al.

It is certified that error appears in the above-indentified patent and that said Letters Patent is hereby corrected as shown below:

Column 11, Claim 9, line 2, delete the number "42" and substitute therefore the number 1.

Column 11, Claim 12, line 2, delete the number "42" and substitute therefore the number 1.

Signed and Sealed this

Eleventh Day of January, 1994

Attest:

BRUCE LEHMAN

*Attesting Officer*     *Commissioner of Patents and Trademarks*